US010272171B2

(12) United States Patent
Lin et al.

(10) Patent No.: US 10,272,171 B2
(45) Date of Patent: Apr. 30, 2019

(54) PORTABLE ELECTRONIC DEVICE WITH A SMART AIR PURIFIER

(71) Applicant: National Cheng Kung University, Tainan (TW)

(72) Inventors: Ming-Yeng Lin, Kaohsiung (TW); Huann-Shyang Lin, Kaohsiung (TW)

(73) Assignee: NATIONAL CHENG KUNG UNIVERSITY, Tainan (TW)

(*) Notice: Subject to any disclaimer, the term of this patent is extended or adjusted under 35 U.S.C. 154(b) by 454 days.

(21) Appl. No.: 15/132,307

(22) Filed: Apr. 19, 2016

(65) Prior Publication Data
US 2017/0106218 A1 Apr. 20, 2017

Related U.S. Application Data

(60) Provisional application No. 62/241,162, filed on Oct. 14, 2015.

(51) Int. Cl.
*A62B 23/00* (2006.01)
*A61L 9/20* (2006.01)
(Continued)

(52) U.S. Cl.
CPC ............... *A61L 9/20* (2013.01); *B01D 53/30* (2013.01); *B03C 3/017* (2013.01); *B03C 3/155* (2013.01); *B03C 3/32* (2013.01); *B03C 3/368* (2013.01); *B03C 3/38* (2013.01); *A62B 18/003* (2013.01); *B01D 53/04* (2013.01); *B01D 53/885* (2013.01); *B01D 2251/104* (2013.01); *B01D 2253/102* (2013.01); *B01D 2253/304* (2013.01);
(Continued)

(58) Field of Classification Search
CPC ........... A61L 9/20; B03C 3/155; A62B 23/00; A62B 23/02
See application file for complete search history.

(56) References Cited

U.S. PATENT DOCUMENTS

2005/0223902 A1 10/2005 Lovell et al.
2009/0229469 A1* 9/2009 Campbell ................. F24F 3/16
96/417
(Continued)

FOREIGN PATENT DOCUMENTS

CN 2667815 Y 12/2004
CN 101191652 A 6/2008
(Continued)

*Primary Examiner* — Timothy A Stanis
(74) *Attorney, Agent, or Firm* — Bacon & Thomas, PLLC

(57) ABSTRACT

A portable electronic device with a smart air purifier is provided with an electronic device body having a display surface, a back surface and a side jointed with the surfaces. The smart air purifier is embedded in the electronic device body. The smart air purifier includes a container, a fan, an air cleaning device, an air quality receiver, a tracking device, an adjustable opening, and a control panel. The container includes an air inlet formed on the back surface, an air outlet formed on the display surface, and an opening formed on the side. The fan draws air from the inlet to provide an airflow. The air cleaning device filters the airflow. The air quality receiver detects quality of the airflow. The tracking device tracks the user. The adjustable opening is disposed at the air outlet of the container. The control panel controls the fan and the adjustable opening.

18 Claims, 9 Drawing Sheets

(51) Int. Cl.
    *B03C 3/155*     (2006.01)
    *B03C 3/32*     (2006.01)
    *B03C 3/36*     (2006.01)
    *B01D 53/30*     (2006.01)
    *B03C 3/017*     (2006.01)
    *B03C 3/38*     (2006.01)
    *A62B 18/00*     (2006.01)
    *B01D 53/04*     (2006.01)
    *B01D 53/88*     (2006.01)

(52) U.S. Cl.
    CPC .. *B01D 2257/502* (2013.01); *B01D 2257/708* (2013.01); *B01D 2257/90* (2013.01); *B01D 2258/06* (2013.01); *B01D 2259/4541* (2013.01); *B01D 2259/804* (2013.01); *B01D 2259/818* (2013.01); *B03C 2201/24* (2013.01)

(56) References Cited

U.S. PATENT DOCUMENTS

| | | | |
|---|---|---|---|
| 2009/0232710 A1* | 9/2009 | Kinsey | A61L 9/03 422/119 |
| 2011/0126828 A1* | 6/2011 | Wu | A62B 7/10 128/201.25 |
| 2015/0352564 A1* | 12/2015 | Genereux | B03C 3/41 96/25 |
| 2015/0355693 A1* | 12/2015 | Chang | G06F 1/203 361/679.48 |

FOREIGN PATENT DOCUMENTS

| | | |
|---|---|---|
| CN | 103528137 A | 1/2014 |
| CN | 104949196 A | 9/2015 |
| CN | 204615902 U | 9/2015 |

\* cited by examiner

PORTABLE ELECTRONIC DEVICE WITH A SMART AIR PURIFIER

BACKGROUND OF THE INVENTION

1. Field of the Invention

The present invention relates to a portable electronic device and, in particular, to a portable electronic device with a smart air purifier.

2. Description of Related Art

Air pollution may result in adverse health effects, especially in highly polluted areas. Air pollution contains two major components, gases and particles. Both of them can be effectively removed by air purifiers.

In one common prior art approach, an air purifier contains a filter, a fan, and a box. In another common prior art approach, an air purifier contains an ionizer, a fan, and a box.

Different devices are currently offered that provide partial solutions for cleaning air. Such devices are either dedicated to particular use or too large to be adapted for other use. Current air purifiers are mostly large and bulky, often fixed in one place and functions best to its surrounding areas. Therefore, when people moves farther away, most of current air purifier's function is restricted. Moreover, wearing respiratory mask can be burdensome to some human subjects.

In the present invention, the smart air purifier 120 shown in FIG. 1 may have small form-factor, wherein the smart air purifier 120 shown in FIG. 1 of the present invention can be arranged in a portable device for supplying fresh air to the user. In comparison with prior art, such as patent application publication number 2005/0223902 invented by Lovell for a "self-powered, wearable personal air purifier". As shown in FIG. 21 of Lovell, the form factor of the Personal Air Purifier (PAP) 10 is much larger than that of the present invention. The Personal Air Purifier (PAP) 10 of Lovell can't be embedded in a portable electronic device whereas the smart air puffier purifier 120 can. In addition, Lovell PAP requires the user to wear a face mask which may be less comfortable than the smart air purifier 120 where the user do not have to wear a face mask.

Moreover, in order to use a portable electronic device to provide purified air, China utility model number CN204615902 disclosed a "mobile phone with negative oxygen ion air purification function" in which a negative oxygen ion generator is installed in a mobile phone to generate negative oxygen ions under the control of a mobile phone controller chip for absorbing harmful gas in the air, and China utility model number CN2667815 disclosed a "mobile phone with an air purification function" in which a mini air purification device is additionally provided in a mobile phone for purifying the air. However, such schemes simply miniaturize the ion generator or the air purifier for being installed in a mobile phone to purify air, which may be insufficient in air purification (i.e., it can't be used to filter some gases and particles) and cannot provide purified air to the preferred spot (e.g., the breathing zone) of the user at a controlled flow rate. This results in less efficiency in air purification as compared to the smart air purifier 120.

Therefore, it is desirable to provide a portable electronic device with a smart air purifier 120 to mitigate and/or obviate the aforementioned problems.

SUMMARY OF THE INVENTION

The objective of the present invention is to provide a portable electronic device with a smart air purifier, which is capable of providing fresh air to the user anytime anywhere.

To achieve the objective, a portable electronic device with a smart air purifier is provided, which comprises an electronic device body, and a smart air purifier. Energy source is installed in the electronic device body to supply power to operate the portable electronic device. The electronic device body has a display surface, a back surface opposite to the display surface, and a side jointed with the display surface and the back surface. The smart air purifier is embedded in the electronic device body and connected to the energy source for its power. The smart air purifier includes a container, a fan, an air cleaning device, an air quality receiver, a tracking device, an adjustable opening, and a control panel. The container is arranged in the electronic device body. The container includes an air inlet formed on the back surface of the electronic device body, an air outlet formed on the display surface of the electronic device body, and an opening formed on the side of the electronic device body. The fan is arranged in the container for drawing air from the inlet to provide an airflow and control the flow rate of the air outlet. The air cleaning device is arranged in the container corresponding to the opening to filter the air flow. The air quality receiver is arranged in the container to detect the quality of the air flow. The tracking device is arranged in the container to track the user. The adjustable opening is disposed at the outlet of the container, wherein the outlet opening size of the adjustable opening is adjustable to control the air flow rate. The control panel is connected to the air quality receiver, the tracking device, the fan, and the adjustable opening to control the fan and the adjustable opening according to information obtained from the air quality receiver and the tracking device.

Other embodiments of the present disclosure will become more apparent from the following detailed description when taken in conjunction with the accompanying drawings.

DETAILED DESCRIPTION OF THE PREFERRED EMBODIMENT

Figure 1:
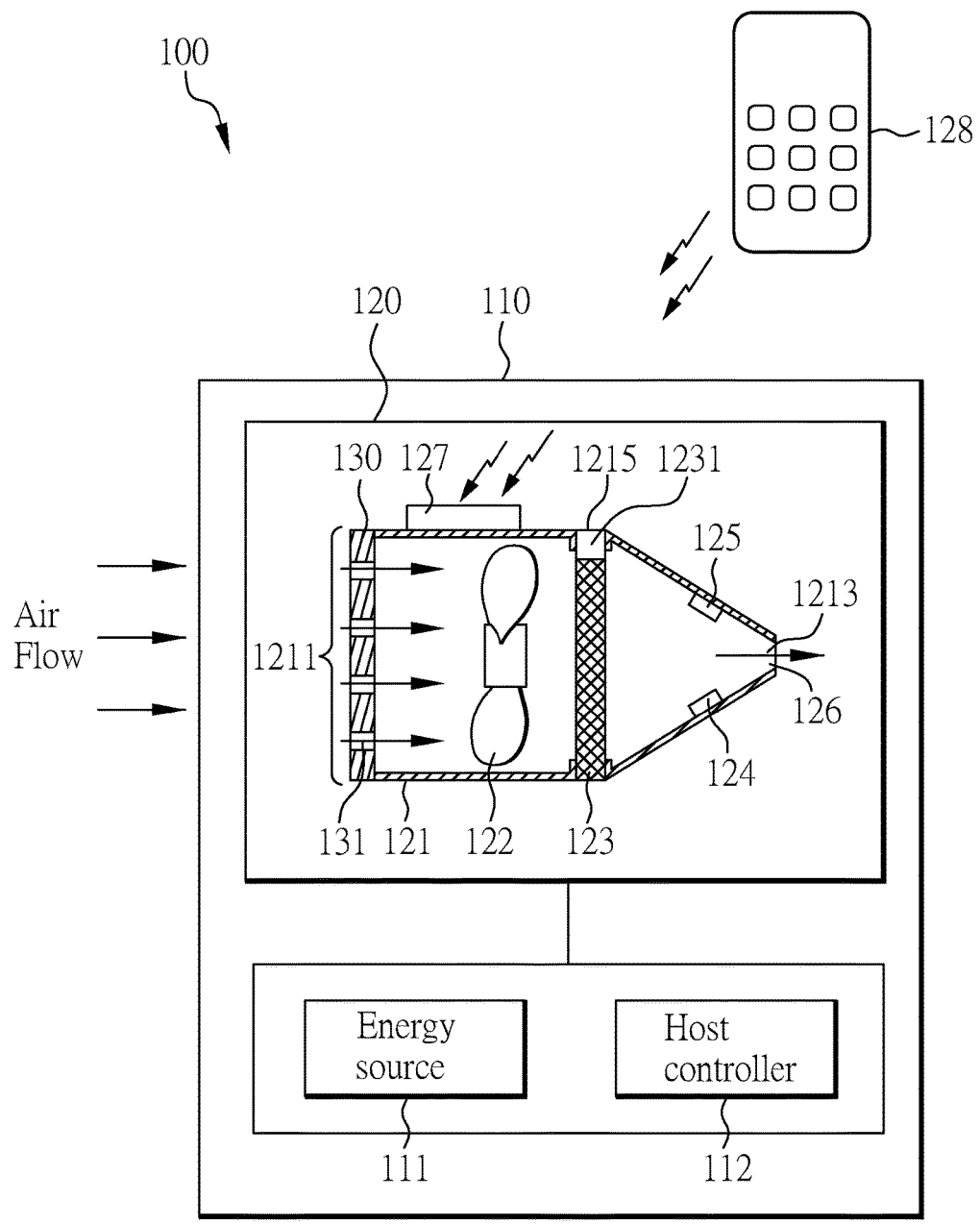
FIG. 1 is a schematic diagram illustrating the functional structure of a portable electronic device with a smart air purifier according to a preferred embodiment of the invention.

FIG. 1 is a schematic diagram illustrating the functional structure of a portable electronic device with a smart air purifier 120 according to a preferred embodiment of the invention. In this embodiment, the portable electronic device can be a smart phone, a notebook computer, a tablet computer, a watch, or the like. The portable electronic device 100 includes an electronic device body 110 and a smart air purifier 120 embedded in the electronic device body 110. The electronic device body 110 has energy source 111 and a host controller 112. The energy source 111 is installed in the electronic device body 110 to supply power to operate the portable electronic device 100 and the host controller 112 is primarily provided to control the functional operation of the portable electronic device 100.

As shown in FIG. 1, the smart air purifier 120 is embedded in the electronic device body 110 and connected to the energy source 111 for its power. The smart air purifier 120 includes a container 121, a fan 122, an air cleaning device 123, an air quality receiver 124, a tracking device 125, an adjustable opening 126 that includes an adjustable lid cover 1261, a control panel 127, a remote control 128, and a back cover 130 with porous holes 131.

Figure 2:
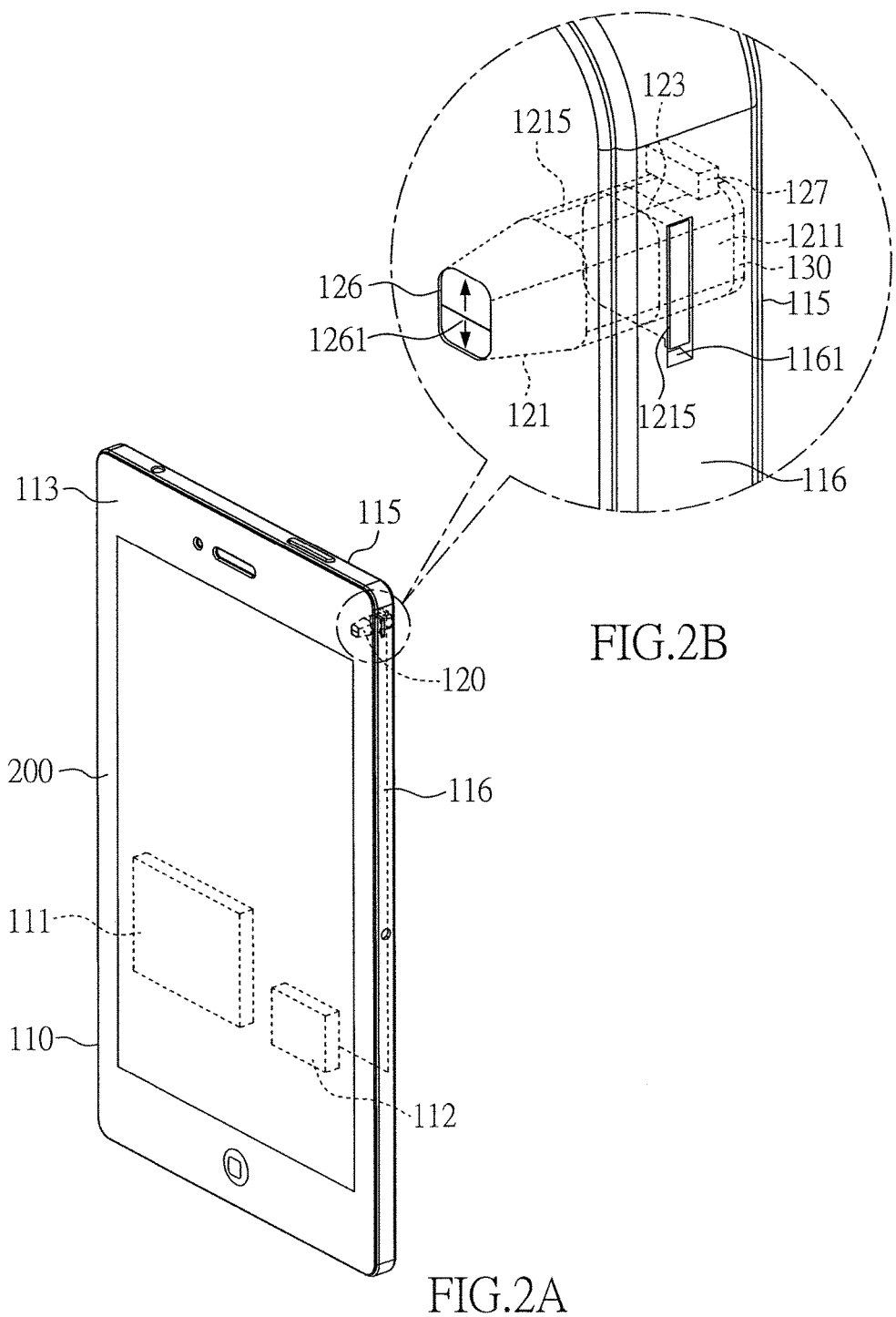
FIG. 2A is a schematic diagram illustrating the physical structure of the portable electronic device with a smart air purifier according to a preferred embodiment of the invention.
FIG. 2B is an enlarged view for illustrating the smart air purifier in the portable electronic device in FIG. 2A.

The container 121 is arranged in the electronic device body 110. The container 121 includes a porous air inlet 1211 formed on the back surface of the electronic device body 110 (as shown in FIG. 2A), an air outlet 1213 formed on the display surface of the electronic device body 110 (as shown in FIG. 2A), and an opening 1215 formed on the side of the electronic device body 110 (as shown in FIG. 2A). The container 121 can be made of any shape, size, and material. In one embodiment, the container 121 is made of fireproof material.

The fan 122 is arranged in the container 121 for drawing air from the air inlet 1221 to provide an airflow and control the flow rate of the air outlet.

The fan 122 is an optional device in the smart air purifier 120. In conditions with little or no airflow entering the smart air purifier 120, the fan 122 is needed to draw in sufficient amount of air to supply the user. In conditions where there is adequate amount of airflow entering the smart air purifier 120 such as the air outlet of the HVAC (Heating Ventilation Air Conditioning) system, the fan 122 is not necessarily needed. The rotating speed of the fan 122 can be controlled by the control panel 127 and/or the remote control 128. The smart air purifier 120 can be installed with one or more fans 122.

The air cleaning device 123 is arranged in the container 121 corresponding to the opening 1215 to filter the air flow. The air cleaning device 123 may include any type or combination of air cleaning elements. The air cleaning device 123 can be designed to remove any type of gas and particle from the air.

In one embodiment, the air cleaning device 123 is an air filter. The air filter can be a High Efficiency Particulate Air (HEPA) filter, an Ultra Low Penetration Air filter (ULPA), a nano-fiber filter, a carbon filter, a gas filter, a catalyst filter, or an anti-microbial filter. Moreover, the air filter can be treated with specific chemicals to remove specific gas or particle.

In another embodiment, the air cleaning device 123 is an ionizer for producing high concentration of charged ions capable of attaching to the particle's surface. Thus, charged particles are more easily collected by some fibers or other surfaces.

In still another embodiment, the air cleaning device 123 is an ultraviolet air purifier which uses ultraviolet light source to eliminate hazardous bioaerosol.

In yet another embodiment, the air cleaning device 123 is an ozone generator for generating ozone to eliminate living organism. Ozone is a powerful oxidant that can obliterate living organism such as bioaerosol. Moreover, ozone can further neutralize many odors.

In yet another embodiment, the air cleaning device 123 is a catalyst filter. The catalyst filter can turn harmful gases such as carbon monoxide to less harmful carbon dioxide. Thus, the smart air purifier 120 can protect the user in hazardous environments such as events of fire.

It should be noted that the air cleaning device 123 may include the ionizer, the ultraviolet air purifier, and the ozone generator. The air cleaning device 123 can be before or after the fan and can be one or many pieces. In another embodiment, the ionizer, the ultraviolet air purifier, and the ozone generator can be built either in the air cleaning device 123 or at any other places of the smart air purifier 120. It is also noted that the air cleaning device 123 can include one or more of the followings: filters, the ionizer, the ultraviolet air purifier, and the ozone generator, as discussed above.

The air cleaning device 123 further includes a differential pressure gauge 1231 to detect the pressure difference of the input airflow of the air cleaning device 123 and the output airflow of the air cleaning device 123. When the pressure difference detected by the differential pressure gauge 1231 is greater than a predetermined threshold, the differential pressure gauge 1231 will send a warning signal to the control panel 127 or the host controller 112 to inform the user to change the air cleaning device 123. The user can replace the old air cleaning device 123 with a new one through the opening 1215. The opening 1215 can also be a removable cap.

The air quality receiver 124 may be an air quality sensor. The air quality receiver 124 is arranged in the container 121 for detecting quality of the airflow. When certain gas or particle level is health hazardous, the fan speed will increase to generate more fresh air. The air quality receiver 124 is preferably a sensor for detecting one or more of the following: PM2.5, PM10, particle number concentration, particle size distribution, or particle chemical composition, gas species, gas concentrations. The detected concentration from the air quality receiver 124 can be sent back to the control panel 127 for data processing.

In another embodiment, the air quality receiver 124 is a gas sensor for detecting ozone, methane, carbon monoxide, carbon dioxide, or Volatile Organic Compounds (VOCs).

In another embodiment, the air quality receiver 124 is a mobile application (APP) for receiving the air quality information from an air quality monitor station.

In another embodiment, the air quality receiver 124 is not used. Instead, local air quality data is received by the portable electronics and the information is sent to the control panel of the smart air purifier.

The tracking device 125 is arranged in the container 121 for tracking the user. The tracking device 125 can track one or more of the followings: body temperature of the user, eye movement of the user, facial expression of the user, body movement of the user, biomarker of the user, and signals sent from the location indication device 710.

That is, the tracking device 125 can track the movement and location of the user, wherein the movement may include eye movement, facial movement, body movement, etc. The tracking device 125 can also calculate the distance between the user's nose and the smart air purifier 120, and can also track the human biomarkers such as human breath. The tracked information can be sent to the control panel 127 for data processing. In one embodiment, the tracking device 125 can track the location and distance of the user's nose relative to the smart air purifier 120. In another embodiment, when the user carries the remote control 128, the tracking device 125 can track the location of the user by tracking the remote control 128 and calculate the distance between the remote control 128 and the smart air purifier 120, this will help determine the air flow rate at the outlet. The tracking device 125 can be one or more devices.

In still another embodiment, the tracking device 125 is an infrared detector to detect the face location of the user.

In still another embodiment, the tracking device 125 can also be a metal sensor to detect the location of the user's metal glasses or the earrings.

In still another embodiment, the tracking device 125 can also be a sensor to detect the place of the location indication device 710 which is attached to the user.

Figures 9A, 9B:
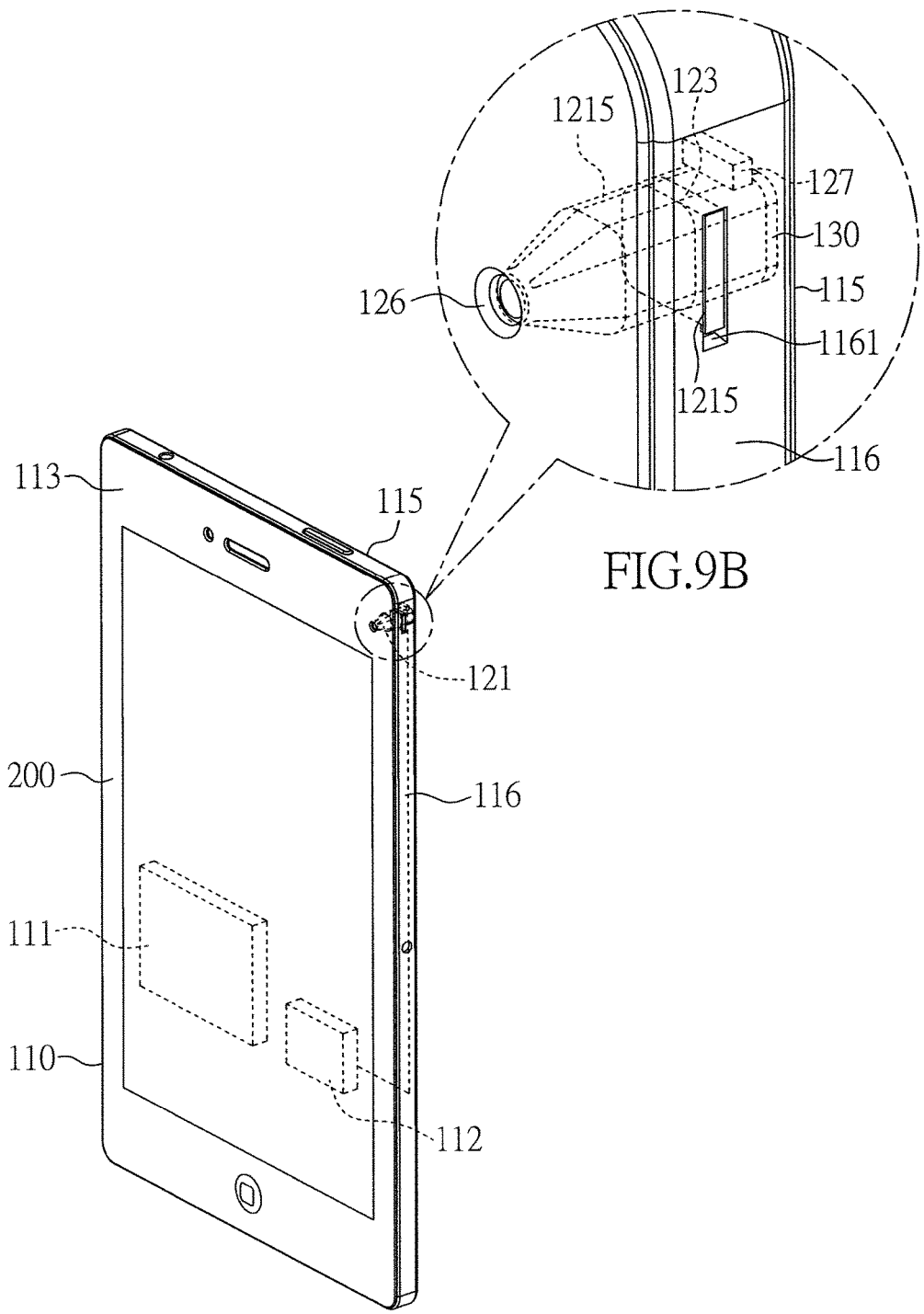
FIG. 9A is a schematic diagram illustrating the physical structure of the portable electronic device with a smart air purifier according to another preferred embodiment of the invention.
FIG. 9B is an enlarged view for illustrating the smart air purifier in the portable electronic device in FIG. 9A.

The adjustable opening 126 is disposed at the air outlet 1213 of the container 121 and has an adjustable lid cover 1261 shown in FIG. 2B. The adjustable opening 126 has an adjustable lid cover 1261 which can adjust the opening size of the lid to control the outlet air flow. In one embodiment, the adjustable opening 126 not only can adjust the flow rate of the airflow by controlling the outlet opening size of the adjustable opening 126 according to the continuity equation, but also can adjust the direction of the airflow. The direction of the airflow and the flow rate are controlled by the control panel 127 and/or the remote control 128. The adjustable opening 126 is an optional device and can be substituted by a fixed opening outlet. That is, there can be none, one or many adjustable openings 126. As shown in FIG. 9A, the adjustable opening 126 can be a nozzle.

The control panel 127 is connected to the air quality receiver 124, the tracking device 125, the fan 122, and the adjustable opening 126 for controlling the fan 122 and the adjustable opening 126 according to the information obtained from the air quality receiver 124 and the tracking device 125.

The control panel 127 receives and processes the information obtained from the air quality receiver 124 and the tracking device 125. The control panel 127 also controls the rotating speed of the fan 122, and the adjustable opening 126 to control the direction of the purified air and the flow rate of the purified air. The control panel can also be embedded in the host controller 112.

The control panel 127 can increase the speed of the fan 122 and decrease the opening size of the adjustable opening 126 when the air quality is poor or when the user is farther away from the smart air purifier. That is, the size of opening of the adjustable opening 126 becomes smaller to ensure that more fresh air is directed toward the user.

On the other hand, when the air quality is better or when the user is closer to the smart air purifier, the control panel 127 can decrease the speed of the fan 122 and increase the outlet opening size of the adjustable opening 126.

The control panel 127 tracks the remote control 128 by using the tracking device 125 so as to direct the air flow to a location where the remote control 128 is located.

The control panel 127 can be a digital or analog device, can be programmable or non-programmable, and can be controlled by the remote control 8.

The remote control 128 is used for remotely controlling the control panel 127. The remote control 128 can communicate with the control panel 127 and operate the smart air purifier 120. The control panel 127 includes controls for setting the rotating speed of the fan 122 for flow rate control, the direction of the adjustable opening 126 for flow direction control, and the air outlet opening size of the adjustable opening 126 for flow rate control. The remote control 128 can be in the form of APPs. There can be one or more remote controls 128

The host controller 112 is arranged in the electronic device body 110 and connected to the control panel 127 for controlling the control panel 127. In one embodiment, the remote control 128 can be in the form of APPs which is operated by the host controller 112.

The back cover 130 with porous holes 131 is arranged in front of the air inlet 121, in which the porous holes 131 can control the air flow rate of the air inlet 121. The air cleaning device 123, the differential pressure gauge 1231, the opening 1215, and the opening 1161 can also be move to the place of the back cover 130 and even replace the back cover 130.

FIG. 2A is a schematic diagram illustrating the physical structure of the portable electronic device with a smart air purifier according to a preferred embodiment of the invention. FIG. 2B is an enlarged view for illustrating the smart air purifier in the portable electronic device in FIG. 2A. As shown in FIG. 2A, the portable electronic device 200 is a smart phone in which the smart air purifier 120 is embedded. In this embodiment, the smart air purifier 120 is arranged at the upper right corner of the smart phone. The electronic device body 110 of the smart phone has a display surface 113, a back surface 115 opposite to the display surface 113, and a side 116 jointed with the display surface 113 and the back surface 115. The porous air inlet 1211 is formed on the back surface 115 of the electronic device body 110. The outlet 1213 is formed on the display surface 113 of the electronic device body 110. The opening 1215 is formed on the side 116 of the electronic device body 110. In the side 116, there is an opening 1161 corresponding to the opening 1215, such that the users can replace the old air cleaning device 123 with a new one through the opening 1215 and the opening 1161.

The smart air purifier 120 can be embedded in any place of the smart phone 200, and it can also be attached to any part of the smart phone 200. The remote control 128 can be in the form of an APP installed in the smart phone 200 or an independent physical remote control. The smart air purifier 120 can supply purified air to the user whenever needed.

Figure 3:
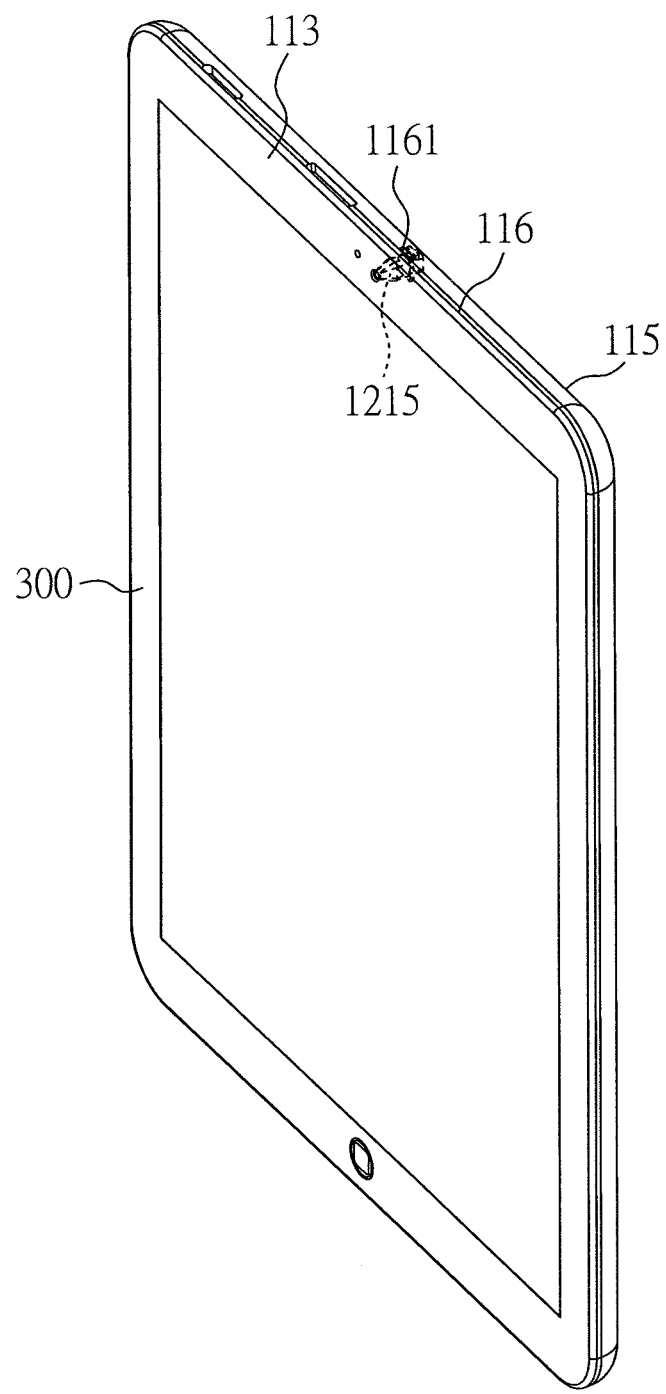
FIG. 3 is another schematic diagram illustrating the physical structure of the portable electronic device with a smart air purifier according to a preferred embodiment of the invention.

FIG. 3 is another schematic diagram illustrating the physical structure of the portable electronic device with a smart air purifier according to a preferred embodiment of the invention. As shown in FIG. 3, the portable electronic device 300 is a tablet computer in which the smart air purifier 120 is embedded. In this embodiment, the smart air purifier 120 is arranged at the top center of the tablet computer. The electronic device body of the tablet computer has a display surface 113, a back surface 115 opposite to the display surface 113, and a side 116 jointed with the display surface 113 and the back surface 115. The physical structure of the smart air purifier 120 of this embodiment is similar to that of FIG. 2B, and thus a detailed description is deemed unnecessary. Similarly, with this smart air purifier 120 arranged at the top center of the tablet computer, the user can replace the old air cleaning device with a new one through the opening 1215 and the opening 1161.

Figure 4:
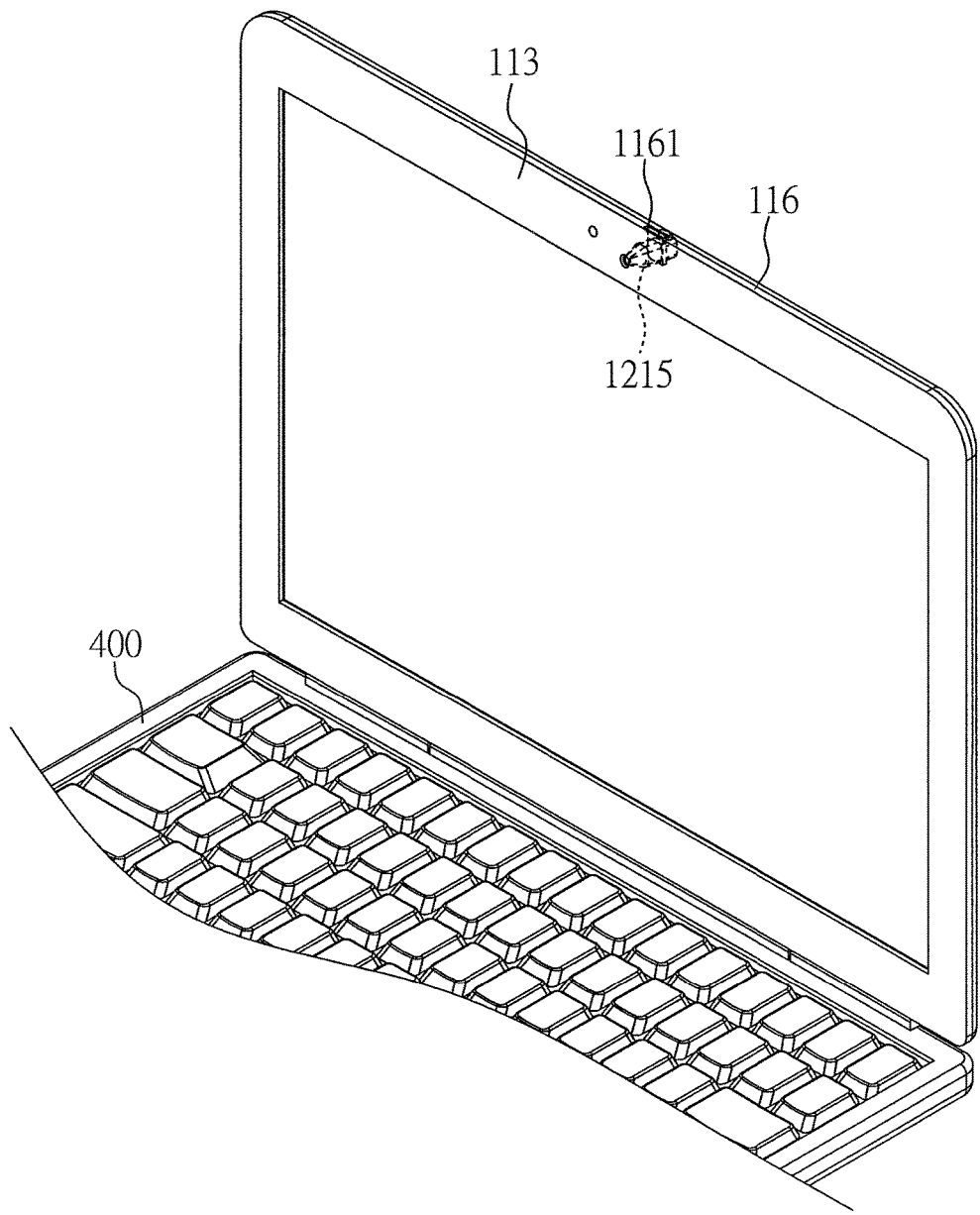
FIG. 4 is still another schematic diagram illustrating the physical structure of the portable electronic device with a smart air purifier according to a preferred embodiment of the invention.

FIG. 4 is still another schematic diagram illustrating the physical structure of the portable electronic device with a smart air purifier according to a preferred embodiment of the invention. As shown in FIG. 4, the portable electronic device 400 is a notebook computer in which the smart air purifier 120 is embedded. In this embodiment, the smart air purifier 120 is arranged at the top center of the display screen of the notebook computer. The electronic device body of the display screen of the notebook computer has a display surface 113, a back surface 115 opposite to the display surface 113, and a side 116 jointed with the display surface 113 and the back surface 115. The physical structure of the smart air purifier 120 of this embodiment is similar to that of FIG. 2B, and thus a detailed description is deemed unnecessary. Similarly, with this smart air purifier 120 arranged at the top center of the display screen of the notebook computer, the user can replace the old air cleaning device with a new one through the opening 1215 and the opening 1161.

Figure 5:
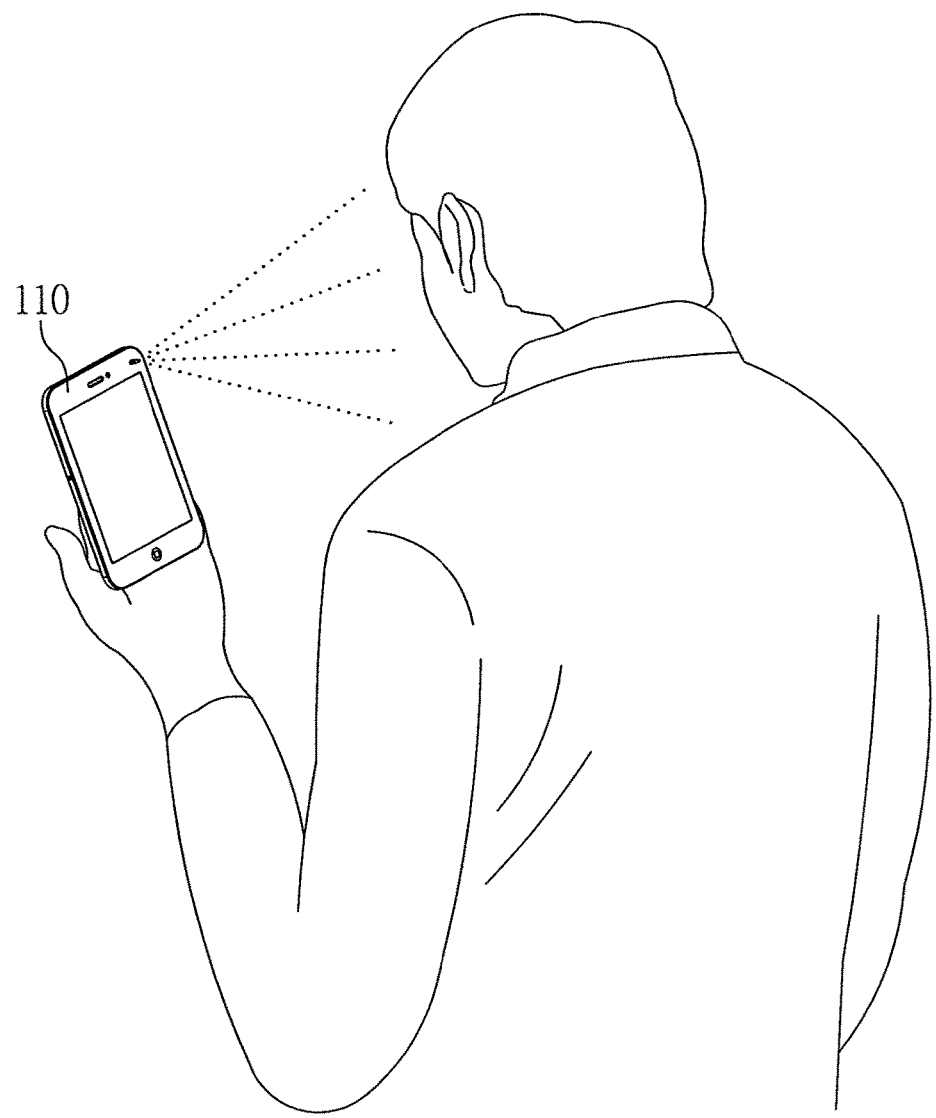
FIG. 5 is a schematic diagram illustrating the usage of the portable electronic device with a smart air purifier according to a preferred embodiment of the invention.

FIG. 5 is a schematic diagram illustrating the usage of the portable electronic device with a smart air purifier according to a preferred embodiment of the invention. As shown in FIG. 5, when using the smart phone 200 with a smart air purifier 120, the user generally faces the display surface 113 of the smart phone 200 so that the smart air purifier 120 can provide fresh air to the user.

Figure 6:
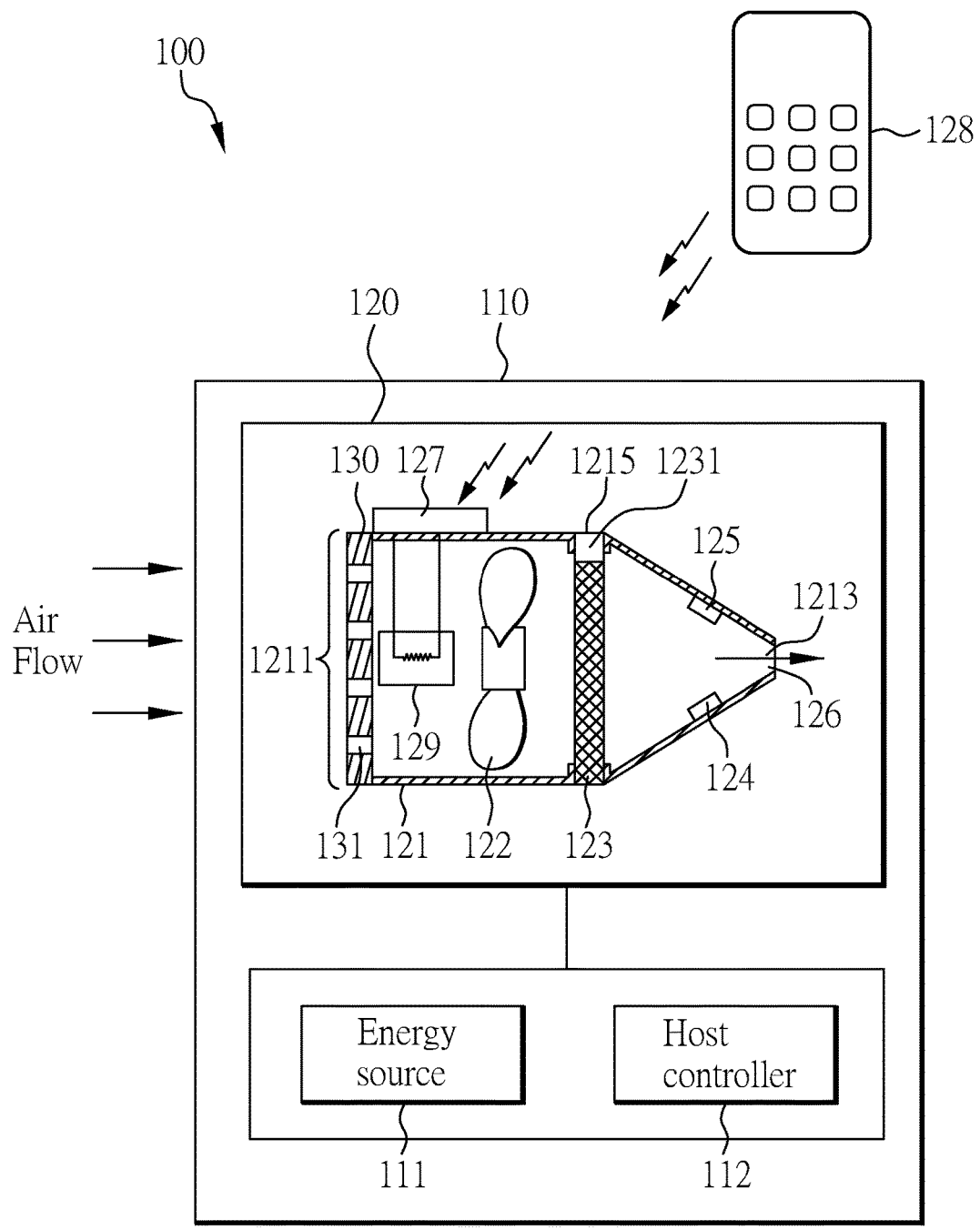
FIG. 6 is a schematic diagram illustrating the functional structure of a portable electronic device with a smart air purifier according to another preferred embodiment of the invention.

FIG. 6 is a schematic diagram illustrating the functional structure of a portable electronic device with a smart air purifier according to another preferred embodiment of the invention. As shown in FIG. 6, this embodiment is similar to that of FIG. 1, except that the smart air purifier 120 further includes a heater 129 which can heat the airflow in winter. In another embodiment, the smart air purifier 120 may include a cooler instead of the heater 129, in which the cooler can cool the airflow in summer.

Figure 7:
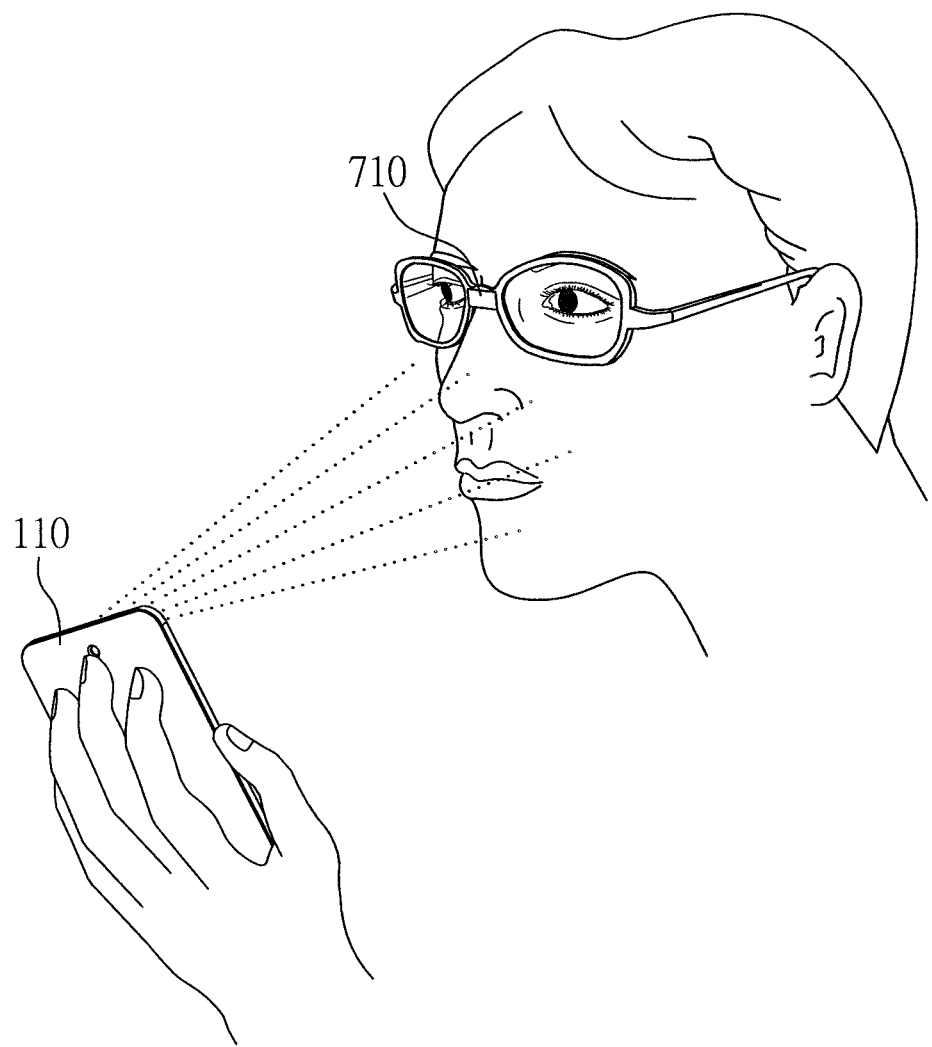
FIG. 7 is another schematic diagram illustrating the usage of the portable electronic device with a smart air purifier according to a preferred embodiment of the invention.

FIG. 7 is another schematic diagram illustrating the usage of the portable electronic device with a smart air purifier 120 according to a preferred embodiment of the invention. As shown in FIG. 7, there is a location indication device 710 disposed at the nose bridge of an eyeglasses of the user. When the tracking device 125 receives the location of the user, the smart air purifier 120 can provide fresh air to the user's breathing zone or any other preferred area. The location indication device 710 may be disposed at a temple of the eyeglasses. The location indication device 710 can be a micro-chip which transmits the wireless beacon to the tracking device 125. In still another embodiment of the invention, the location indication device 710 may be attached to other parts of the glass. In still another embodiment of the invention, the location indication device 710 may be disposed at an earring of the user.

Figure 8:
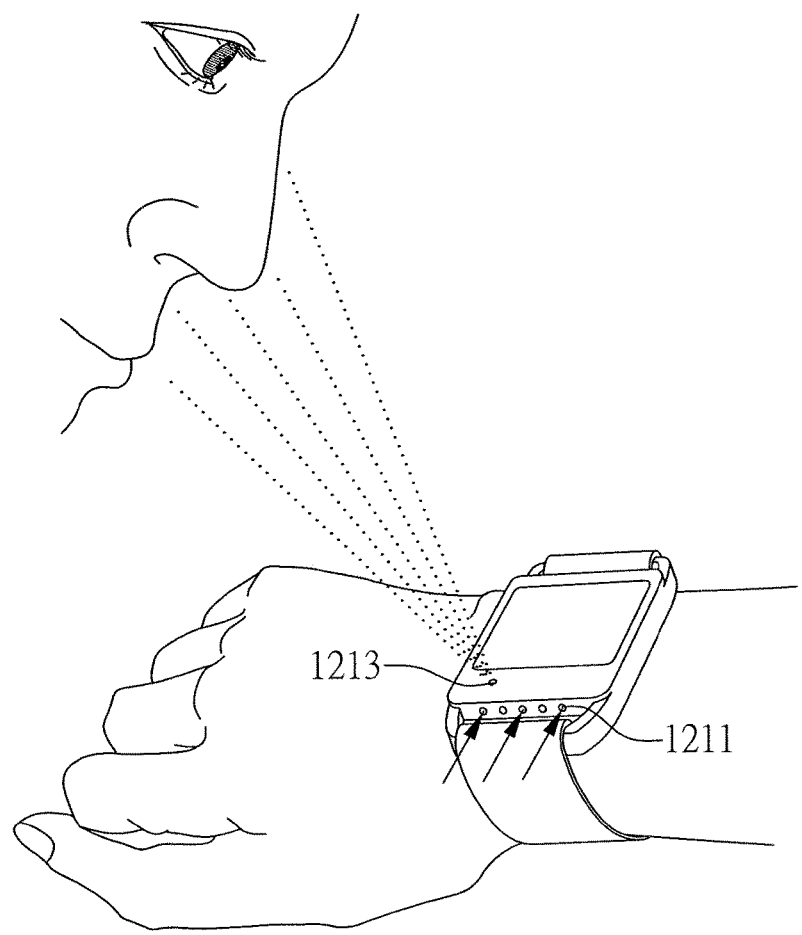
FIG. 8 is still another schematic diagram illustrating the usage of the portable electronic device with a smart air purifier according to a preferred embodiment of the invention.

FIG. 8 is still another schematic diagram illustrating the usage of the portable electronic device with a smart air purifier according to a preferred embodiment of the invention. As shown in FIG. 8, the portable electronic device is a watch 800 in the embodiment and, when using a watch 800 with a smart air purifier 120, the user generally faces the display surface 810 of the watch 800 so that the smart air purifier 120 can effectively provide the fresh air to the user.

FIG. 9A is a schematic diagram illustrating the physical structure of the portable electronic device with a smart air purifier according to another preferred embodiment of the invention. As shown in FIG. 9A, the adjustable opening 126 can be replaced by a nozzle. FIG. 9B is an enlarged view for illustrating the smart air purifier in the portable electronic device in FIG. 9A In view of the foregoing, it is known that the portable electronic device with a smart air purifier 120 of the present invention can be a small form factor to provide the user with the convenience of carrying, as shown by FIG. 2A to FIG. 8, and the fresh air can be supplied to the user irrespective of user location.

Although the present disclosure has been explained in relation to its various embodiments, it is to be understood that many other possible modifications and variations can be made without departing from the spirit and scope of the invention as hereinafter claimed.

What is claimed is:

1. A portable electronic device with a smart air purifier, comprising:
    an electronic device body in which an energy source is installed to supply power to operate the portable electronic device, the electronic device body having a display surface, a back surface opposite to the display surface, and a side jointed with the display surface and the back surface; and
    a smart air purifier embedded in the electronic device body and connected to the energy source to receive power to operate, the smart air purifier including:
    a container arranged in the electronic device body, the container including an air inlet formed on the back surface of the electronic device body, an outlet formed on the display surface of the electronic device body, and an opening formed on the side of the electronic device body;
    a fan arranged in the container for drawing air from the inlet to provide an airflow and control a flow rate of the air outlet;
    an air cleaning device arranged in the container corresponding to the opening for filtering the airflow;
    an air quality receiver arranged in the container for receiving a surrounding environment's air quality;
    a tracking device arranged in the container for tracking a user;
    an adjustable opening disposed at the outlet of the container, wherein an outlet opening size is adjustable for controlling the flow rate; and
    a control panel connected to the air quality receiver, the tracking device, the fan, and the adjustable opening for controlling the fan and the adjustable opening according to information obtained from the air quality receiver and the tracking device.

2. The portable electronic device with a smart air purifier as claimed in claim 1, wherein the adjustable opening is controlled to adjust the flow rate and a direction of the airflow.

3. The portable electronic device with a smart air purifier as claimed in claim 1, wherein the control panel increases a speed of the fan and decreases the outlet opening size of the adjustable opening when the air quality is poor or when the user is farther away from the smart air purifier, and the control panel decreases the speed of the fan and increases the outlet size of the adjustable opening when the air quality is good or when the user is closer to the smart air purifier.

4. The portable electronic device with a smart air purifier as claimed in claim 1, wherein the tracking device is configured to track one or more of the following: body temperature of the user, eye movement of the user, facial expression of the user, body movement of the user, biomarker of the user, and specific materials people wear.

5. The portable electronic device with a smart air purifier as claimed in claim 1, wherein the adjustable opening is a nozzle.

6. The portable electronic device with a smart air purifier as claimed in claim 1, wherein the air cleaning device is an air filter.

7. The portable electronic device with a smart air purifier as claimed in claim 6, wherein the air filter is a High Efficiency Particulate Air (HEPA) filter, an Ultra Low Penetration Air filter (ULPA), a nano-fiber filter, a carbon filter, a gas filter, a catalyst filter, or an anti-microbial filter.

8. The portable electronic device with a smart air purifier as claimed in claim 1, wherein the air cleaning device is an ionizer for producing high concentration of charged ions capable of attaching to a particle's surface.

9. The portable electronic device with a smart air purifier as claimed in claim 1, wherein the air cleaning device is an ultraviolet air purifier which uses an ultraviolet light source to eliminate living organisms.

10. The portable electronic device with a smart air purifier as claimed in claim 1, wherein the air cleaning device is a catalyst filter which is configured to turn carbon monoxide to carbon dioxide.

11. The portable electronic device with a smart air purifier as claimed in claim 1, wherein the air quality receiver is a sensor for detecting one or more of the following: PM2.5, PM10, particle number concentration, particle size distribution, particle chemical composition, gas concentration, gas composition, ozone, methane, carbon monoxide, carbon dioxide, and Volatile Organic Compounds (VOCs).

12. The portable electronic device with a smart air purifier as claimed in claim 1, wherein the air quality receiver is a mobile application (APP) for receiving air quality information from an air quality monitor station.

13. The portable electronic device with a smart air purifier as claimed in claim 1, wherein local air quality is directly sent to the portable electronic device and transferred to the control panel of the smart air purifier without using the air quality receiver.

14. The portable electronic device with a smart air purifier as claimed in claim 1, further comprising:
 a remote control for remotely controlling the control panel.

15. The portable electronic device with a smart air purifier as claimed in claim 14, wherein the control panel tracks the remote control by the tracking device so as to direct the air flow to a location where the remote control is disposed.

16. The portable electronic device with a smart air purifier as claimed in claim 1, further comprising a location indication device which is configured to be attached to the user, the tracking device is configured to track the location indication device and send a signal back to the control panel, and the control panel is configured to send out signals to direct the air flow to where the location indication device is disposed.

17. The portable electronic device with a smart air purifier as claimed in claim 1, further comprising:
 a host controller arranged in the electronic device body and connected to the control panel for controlling the control panel.

18. The portable electronic device with a smart air purifier as claimed in claim 1, wherein the portable electronic device is a smart phone, a notebook computer, or a tablet computer.

* * * * *